United States Patent [19]

Rubin et al.

[11] Patent Number: 5,474,993
[45] Date of Patent: Dec. 12, 1995

[54] LACTAM INHIBITORS OF CHOLESTEROL ESTERASE

[75] Inventors: Byron Rubin, Honeoye Falls; Kenneth C. Mattes; Terrence C. Mungal, both of Rochester, all of N.Y.

[73] Assignee: Sterling Winthrop, Inc., New York, N.Y.

[21] Appl. No.: 259,593

[22] Filed: Jun. 14, 1994

[51] Int. Cl.⁶ .................... C07D 499/00; A61K 31/425
[52] U.S. Cl. .................... 514/192; 514/197; 540/304; 540/310; 540/312
[58] Field of Search ................... 514/192, 197; 540/310, 304

[56] References Cited

U.S. PATENT DOCUMENTS

| | | | |
|---|---|---|---|
| 3,311,638 | 3/1967 | Wolfe | 260/306.7 |
| 5,053,502 | 10/1991 | Hue et al. | 540/304 |
| 5,132,300 | 7/1992 | Volkmann et al. | 540/310 |

*Primary Examiner*—Nicholas Rizzo
*Attorney, Agent, or Firm*—William J. Davis; Paul E. Dupont

[57] ABSTRACT

The present invention is related to compounds which inhibit pancreatic cholesterol esterase. The compounds have the formula:

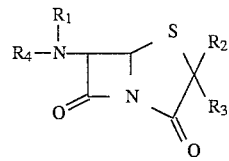

wherein
$R^1$ is H or $C_{1-6}$ alkyl;
$R^2$ is H or $C_{1-6}$ alkyl;
$R^3$ is H or $C_{1-6}$ alkyl;
X is $CHR^6$, S or O;
$R^6$ is H or $C_{1-6}$ alkyl;
$R^4$ is a hydrophobic moiety; and pharmaceutically acceptable salts thereof.

12 Claims, No Drawings

LACTAM INHIBITORS OF CHOLESTEROL ESTERASE

FIELD OF THE INVENTION

This invention relates to new lactam derivatives which inhibits human pancreatic enzyme cholesterol esterase. More particularly, this invention relates to substituted 7-oxo-6-amino-4-thia-1 azabicyclo[3.2.0]heptanes.

BACKGROUND OF THE INVENTION

Pancreatic cholesterol esterase (CEase) is a lipolytic enzyme that catalyzes the hydrolysis of cholesteryl esters, phospholipids and triacylglycerols in the intestinal tract. The enzyme may play a role in the absorption of dietary cholesterol across the intestinal mucosa and eventually into the bloodstream.

Since CEase is required for the absorption of dietary fatty acids, dietary cholesterol, cholesterol esters and bile derived cholesterol into the bloodstream, CEase inhibitors may serve as hypolipidemic, hypocholesterolaemic and hypocaloric agents. Such treatments would be useful in the treatment of hypercholesterolaemia and obesity, health problems that afflict one-third of Americans. It is also a known risk factor in diabetes, arteriosclerosis, atherosclerosis and other life threatening diseases.

U.S. Pat. No. 4,189,438 discloses that a natural product, esterastin, a lactone, inhibits cholesterol esterase and other esterases.

U.S. Pat. No. 4,202,824 discloses that derivatives of esterastin also are active as inhibitors of cholesterol esterase.

U.S. Pat. No. 5,093,371 discloses naphthyl ketone inhibitors of cholesterol esterase.

The prevention of absorption of cholesterol has been largely unexploited as a pharmacological method of treatment of arteriosclerosis. One way of preventing absorption of cholesterol is to cover the walls of the intestinal tract with something which prevents absorption of cholesterol through the intestinal mucosa. This, however, is difficult and not practical because it inhibits the normal digestive process. A far more effective approach would be to develop CEase inhibitors with demonstrated capability of blocking cholesterol absorption. These inhibitors could then be introduced into the alimentary tract through appropriate delivery systems where it would then function to block cholesterol absorption.

This invention is predicated upon the discovery of certain novel CEase inhibitors which successfully block cholesterol absorption, to their use for decreasing the absorption of dietary cholesterol and other fats, and to a pharmaceutical composition comprising the active compound.

SUMMARY OF THE INVENTION

The present invention is related to compounds which inhibit pancreatic cholesterol esterase. The compounds have the formula:

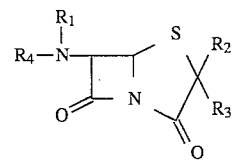

wherein
$R^1$ is H or $C_{1-6}$ alkyl;
$R^2$ is H or $C_{1-6}$ alkyl;
$R^3$ is H or $C_{1-6}$ alkyl;
X is $CHR^6$, S or O;
$R^6$ is H or $C_{1-6}$ alkyl;
$R^4$ is a hydrophobic moiety; and pharmaceutically acceptable salts thereof.

The present invention also relates to a method of treating high serum cholesterol levels. The method comprises administering to a patient needing such treatment, a pharmaceutically effective amount of the compound of the invention.

The invention also relates to pharmaceutical compositions comprised of a pharmaceutically effective mount of a compound of the invention and a pharmaceutically acceptable carrier.

DETAILED DESCRIPTION OF THE INVENTION

The present invention is related to compounds which inhibit pancreatic cholesterol esterase. The compounds have the formula:

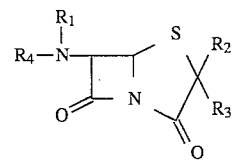

wherein
$R^1$ is H or $C_{1-6}$ alkyl;
$R^2$ is H or $C_{1-6}$ alkyl;
$R^3$ is H or $C_{1-6}$ alkyl;
X is $CHR^6$, S or O;
$R^6$ is H or $C_{1-6}$ alkyl;
$R^4$ is a hydrophobic moiety; and pharmaceutically acceptable salts thereof.

Preferred are compounds with the structure:

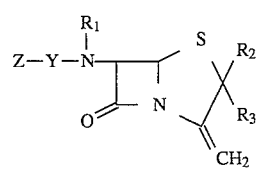

wherein
$R_1$ is H or $C_{1-3}$ alkyl;
$R_2$ is H or $C_{1-3}$ alkyl;
$R_3$ is H or $C_{1-3}$ alkyl;

Y is a chemical bond,

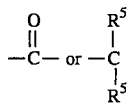

wherein $R_5$ is $C_{1-3}$ alkyl;

Z is $C_{1-6}$ alkyl, $C_{3-8}$ cyclo alkyl, phenyl, phenyl $C_{1-6}$ alkyl, phenyloxy $C_{1-6}$ alkyl, bicylic aryl, fused cyclo $C_{3-8}$ alkyl phenyl, fused phenyl cyclo $C_{3-8}$ alkyl, tricyclic aryl, phenoxyphenyl, or

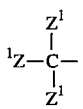

wherein each $Z^1$ is phenyl or bicyclic aryl, and
wherein any of the ring structures can be mono or di substituted with $C_{1-3}$ alkyl or $C_{3-8}$ cyclo alkyl;

and pharmaceutically acceptable salts thereof.
More preferred are compounds of the structure:

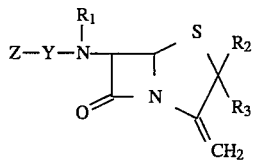

wherein the Y and Z are as above.
Even more preferred are the following compounds:
a (5R,6R)-3,3-dimethyl-2-methylene-7-oxo-6-[(1,2,3,4-tetrahydro-2-naphthalenylcarbonyl)amino]-4-thia-1-azabicyclo[3.2.0]heptane;
b (5R,6R)-3,3-dimethyl-2-methylene-7-oxo-6-[(1-oxopropyl)amino]-4-thia-1-azabicyclo[3.2.0]heptane;
c (5R,6R)-3,3-dimethyl-2-methylene-7-oxo-6-[(1-oxobutyl)amino]-4-thia-1-azabicyclo[3.2.0]heptane;
d (5R,6R)-3,3-dimethyl-2-methylene-7-oxo-6-[(1-oxopentyl)amino]-4-thia-1-azabicyclo[3.2.0]heptane;
e (5R,6R)-3,3-dimethyl-2-methylene-7-oxo-6-[(1-oxohexyl)amino]-4-thia-1-azabicyclo[3.2.0]heptane;
f (5R,6R)-3,3-dimethyl-2-methylene-7-oxo-6-[(1-oxoheptyl)amino]-4-thia-1-azabicyclo[3.2.0]heptane;
g (5R,6R)-3,3-dimethyl-2-methylene-7-oxo-6-[(1-oxo-octyl)amino]-4-thia-1-azabicyclo[3.2.0]heptane;
h (5R,6R)-3,3-dimethyl-2-methylene-7-oxo-6-[[1-oxo-2,2-dimethyl-4-(2',5'-dimethylphenoxy)butyl]amino]-4-thia-1-azabicyclo[3.2.0]heptane;
i (5R,6R)-3,3-dimethyl-2-methylene-7-oxo-6-[[1-oxo-2,2-dimethyl-2(4'-cyclopropylphenoxy)ethyl]amino]-4-thia-1-azabicyclo[3.2.0]heptane;
j (5R,6R)-3,3-dimethyl-2-methylene-7-oxo-6-[[(3,4-cycloheptenophenyl)carbonyl]amino]-4-thia-1-azabicyclo[3.2.0]heptane;
k (5R,6R)-3,3-dimethyl-2-methylene-7-oxo-6-[[(1,2,3,4-tetrahydronaphthalen-6-yl)carbonyl]amino]-4-thia-1-azabicyclo-[3.2.0]heptane;
l (5R,6R)-3,3-dimethyl-2-methylene-7-oxo-6-[ [(cyclohexyl)carbonyl]amino]-4-thia-1-azabicyclo[3.2.0]heptane;
m (5R,6R)-3,3-dimethyl-2-methylene-7-oxo-6-(phenylacetyl)amino-4-thia-1-azabicyclo[3.2.0]heptane;
n (5R,6R)-3,3-dimethyl-2-methylene-7-oxo-6-[(1-oxo-3-phenylpropyl)amino]-4-thia-1-azabicyclo[3.2.0]heptane;
o (5R,6R)-3,3-dimethyl-2-methylene-7-oxo-6-[(1-oxo-4-phenylbutyl)amino]-4-thia-1-azabicyclo[3.2.0]heptane;
p (5R,6R)-3,3-dimethyl-2-methylene-7-oxo-6-[(1-oxo-5-phenylpentyl)amino]-4-thia-1-azabicyclo[3.2.0]heptane;
q (5R,6R)-3,3-dimethyl-2-methylene-7-oxo-6-[(1-oxo-6-phenylhexyl)amino]-4-thia-1-azabicyclo[3.2.0]heptane;
r (5R,6R)-3,3-dimethyl-2-methylene-7-oxo-6-[(1-oxo-7-phenylheptyl)amino]-4-thia-1-azabicyclo[3.2.0]heptane;
s (5R,6R)-3,3-dimethyl-2-methylene-7-oxo-6-[(1-oxo-8-phenyloctyl)amino]-4-thia-1-azabicyclo[3.2.0]heptane;
t (5R,6R)-3,3-dimethyl-2-methylene-7-oxo-6-[(1-oxo-9-phenylnonyl)amino]-4-thia-1-azabicyclo[3.2.0]heptane;
u (5R,6R)-3,3-dimethyl-2-methylene-7-oxo-6-[(2-naphthalenylcarbonyl)-amino]-4-thia-1-azabicyclo[3.2.0]heptane;
v (5R,6R)-3,3-dimethyl-2-methylene-7-oxo-6-[(3'-phenoxyphenylcarbonyl)-amino]-4-thia-1-azabicyclo[3.2.0]heptane;
w (5R,6R)-3,3-dimethyl-2-methylene-7-oxo-6-[(2-anthracenylcarbonyl)-amino]-4-thia-1-azabicyclo[3.2.0]heptane;
x (5R,6R)-3,3-dimethyl-2-methylene-7-oxo-6-(1,1-dimethyl-2,2,2-triphenylethyl)amino-4-thia-1-azabicyclo[3.2.0]heptane;
y (5R,6R)-3,3-dimethyl-2-methylene-7-oxo-6-[(1,1-diethylpropyl)amino]-4-thia-1-azabicyclo[3.2.0]heptane;
z (5R,6R)-3,3-dimethyl-2-methylene-7-oxo-6-[[[(3'-phenoxy)phenyl-1,1-dimethyl]methyl]amino]-4-thia-1-azabicyclo[3.2.0]heptane;
aa (5R,6R)-3,3-dimethyl-2-methylene-7-oxo-6-[(N-methyl-N-triphenylmethyl)amino]-4-thia-1-azabicyclo[3.2.0] heptane;
ab (5R,6R)-3,3-dimethyl-2-methylene-7-oxo-6-[[[1,1-(di-2'-naphthalenyl)-1-(1'-naphthalenyl)]methyl]amino]-4-thia-1-azabicyclo[3.2.0]heptane;
ac (5R,6R)-3,3-dimethyl-2-methylene-7-oxo-6-[(N-methyl-N-propyl)amino]-4-thia-1-azabicyclo[3.2.0]heptane;
ad (5R,6R)-3,3-dimethyl-2-methylene-7-oxo-6-[(N-methyl-N-butyl)amino]-4-thia-1-azabicyclo[3.2.0]heptane;
ae (5R,6R)-3,3-dimethyl-2-methylene-7-oxo-6-[(N-methyl-N-pentyl)amino]-4-thia-1-azabicyclo[3.2.0]heptane;
af (5R,6R)-3,3-dimethyl-2-methylene-7-oxo-6-[(N-methyl-N-hexyl)amino]-4-thia-1-azabicyclo[3.2.0]heptane;
ag (5R,6R)-3,3-dimethyl-2-methylene-7-oxo-6-[(N-methyl-N-heptyl)amino]-4-thia-1-azabicyclo[3.2.0]heptane;
ah (5R,6R)-3,3-dimethyl-2-methylene-7-oxo-6-[(N-methyl-N-octyl)amino]-4-thia-1-azabicyclo[3.2.0]heptane;
ai (5R,6R)-3,3-dimethyl-2-methylene-7-oxo-6-[(N-propyl)amino]-4-thia-1-azabicyclo[3.2.0]heptane;
aj (5R,6R)-3,3-dimethyl-2-methylene-7-oxo-6-[(N-butyl)amino]-4-thia-1-azabicyclo[3.2.0]heptane;
ak (5R,6R)-3,3-dimethyl-2-methylene-7-oxo-6-[(N-pentyl)amino]-4-thia- 1-azabicyclo[3.2.0]heptane;
al (5R,6R)-3,3-dimethyl-2-methylene-7-oxo-6-[(N-hexyl)amino]-4-thia-1-azabicyclo[3.2.0]heptane;
am (5R,6R)-3,3-dimethyl-2-methylene-7-oxo-6-[(N-heptyl)amino]-4-thia-1-azabicyclo[3.2.0]heptane; and
an (5R,6R)-3,3-dimethyl-2-methylene-7-oxo-6-[(N-octyl)amino]-4-thia-1-azabicyclo[3.2.0]heptane.

Especially preferred are:
(5R,6R)-3,3-dimethyl-2-methylene-7-oxo-6-tritylamino-4-thia-1azabicyclo[3.2.0]heptane and
(5R,6R)-3,3-dimethyl-2-methylene-7-oxo-6-[2,2,2-triphenylacetoamido-4-thia-1-azabicyclo[3.2.0]heptane.

As employed above and throughout the disclosure, the following terms, unless otherwise indicated, shall be understood to have the following meanings:

"Alkyl" and "Alkoxy" mean monovalent aliphatic radicals, including branched chain radicals, of from one to ten carbon atoms, preferably one to six carbon atoms, and most preferably one to three carbon atoms. Thus, the lower-alkyl moiety of such groups include, for example, methyl, ethyl, propyl, isopropyl, n-butyl, sec-butyl, t-butyl, n-pentyl, 2-methyl-3-butyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, 1,1,3,3-tetramethylpentyl, 1,1-dimethyloctyl and the like.

"Cycloalkyl" means carbocyclic rings having from three to eight ring carbon atoms including cyclopropyl, cyclobutyl, cyclopentyl, cyclohexyl and cyclooctyl which may be substituted on any ring carbon atom thereof by one or more lower-alkyl groups, lower-alkoxy groups or halogens.

"Aryl" means an aromatic hydrocarbon radical having six to fourteen carbon atoms and includes phenyl, bicyclic aryl and tricyclic aryl. The aryl may be partially saturated. The preferred aryl groups are phenyl, substituted phenyl, naphthyl or substituted naphthyl substituted by from one to three, the same or different members of the group consisting of alkyl, cycloalkyl, halogen, hydroxy-alkyl, alkoxy alkyl and hydroxy.

"Aryloxy" refers to an aryl-O-group. The preferred aryloxy group is phenoxy.

As used herein, the term "pharmaceutically acceptable salts" include the acid and base addition salts.

The term "acid addition salts" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The term "base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts derived from pharmaceutically acceptable organic non-toxic bases including salts of primary, secondary, and tertiary amines, substituted amines, including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tripropylamine, dicyclohexylamine, lysine, arginine, histidine, caffeine, procaines, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline and caffeine.

The compounds are novel and have valuable pharmacological properties. In particular, they inhibit pancreatic enzyme cholesterol esterase and can be used in the control or prevention of obesity and hyperlipaemia.

Another pharmacological property of the compounds is as inhibitors of physiologically significant serine proteases. These proteases include but are not limited to serine proteases isolated from human neutrophils (e.g., PMN elastase, PR3) and proteins isolated from human pancreas (e.g., trypsin and elastase).

The present invention is also concerned with pharmaceutical compositions for preventing and treating obesity or hyperlipaemia comprising a compound of the invention and a pharmaceutically acceptable carrier material.

The invention also concerns methods for preventing or treating obesity and hyperlipaemia in an affected mammal wherein a compound of the invention is in an amount which is effective in treating or preventing obesity or hyperlipaemia.

The pharmaceutical composition of this invention may be formulated as conventional orally administerable forms such as tablets, capsules, powders, solutions and suspensions, either by admixing an amount of a new compound of this invention with a conventional pharmaceutically acceptable solid carrier such as starch, sucrose, talc or calcium carbonate or by dissolving or suspending an mount of a new compound of this invention in a pharmaceutically acceptable liquid carrier such as ethanol or water. The proportion of the active compound of this invention to the solid or liquid carrier may be chosen appropriately depending on the form of the orally administerable formulation prepared and usually may be in a ratio of from 1:1 to 1:100 by weight.

The invention also is directed to a commercially-produced foodstuff comprising a compound of the invention admixed with a material suitable for consumption.

The pharmaceutical composition of this invention may also be formulated into injectable solutions or suspensions by dissolving or suspending the active compound at a suitable level of from 0.1% to 10% by weight into a physiological saline solution or other conventional pharmaceutically acceptable liquid vehicle such as Ringer's solution, with or without aid of a suitable dispersion agent. The injectable solution or suspension so prepared may be given, e.g., by intravenous injection, intramuscular injection or intraperitoneal injection.

It will be appreciated that the actual preferred dosage of the active compound of this invention used will vary according to the particular composition formulated for administration, the mode of administration and the particular disease to be treated. Many factors that modify the action of the drug of this invention will be taken into account by one skilled in the art, for example, age, body, weight, sex, diet, time of administration, route of administration, rate of excretion, drug combinations, reaction sensitivities and severity of the disease. Generally, about 0.5 mg/kg to about 100 mg/kg of the active compound is given daily to an adult person. Optimal dosages for a given set of conditions of a patient can be ascertained by one skilled in the art using conventional dosage determination tests in view of the above guidelines.

It is believed that using the preceding description and without further elaboration, one skilled in the art can utilize the concept of this invention to its full extent. The following preferred specific embodiments are, therefore, to be construed as merely illustrative of this invention.

EXAMPLE 1

A. Preparation of 3,3 dimethyl-2-carboxy-7-oxo-6-tritylamino-4-thia-1-azabicyclo[3.2.0]heptane, diethylamine salt. (Tri-6-APA.NHEt$_2$).

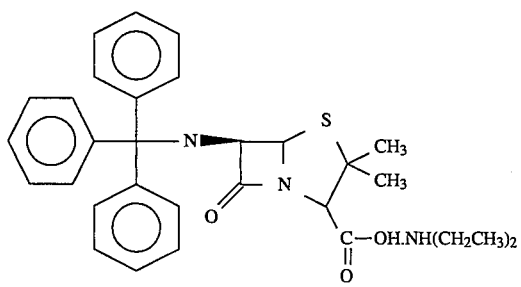

To a 500 ml three-necked round bottom flask is added (+)-6-aminopenicillanic acid (49.7 grams, 0.23 moles, 6-APA, Aldrich), 90 milliliters of water and 185 milliliters of isopropyl alcohol and the slurry/mixture stirred magnetically and cooled to 5° C.

Diethylamine (36.57 grams, 51.7 ml, 0.5 moles) is added dropwise, over 30 minutes, to the magnetically stirred slurry/mixture which becomes a homogeneous solution at the end of the addition. The stirred solution is then cooled to −5° C. and solid triphenylmethyl chloride (195.1 grams, 0.75 moles) is added, in portions, over 75 minutes while maintaining an internal temperature of −5° C.

The reaction mixture is allowed to warm to room temperature, stirred for one hour at room temperature, and then cooled to 0° C. Water (600 ml) is added to the reaction mixture over 20 minutes, and the resulting precipitate removed by vacuum filtration through Supercel followed by a water wash (100 ml).

The filtrate is stirred magnetically, and the pH adjusted to four (4) by the dropwise addition of a 10% aqueous phosphoric acid solution (ca. 55 ml). The resulting precipitate is filtered off using a sintered glass funnel, washed with cold water and dried under vacuum, overnight to yield, quantitatively, a crude, off-white solid product.

H-NMR (CDCl$_3$, TMS, ppm): 7.5 (d,6H) 7.25 (m,9H) 4.41 (d,2H) 4.22 (s, 1H) 2.9 (q,4H) 2.3 (b, ca. 3H); amine salt 1.5 (s,3H) 1.36 (m, 9H).

B. Preparation of 3,3 dimethyl-2-hydroxymethyl-7-oxo-6-tritylamino-4-thia-1-azabicyclo[3.2.0]heptane, (Tri-6-AP-CH2OH).

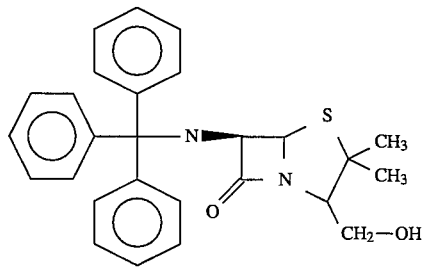

To a 500 ml three-necked round bottom flask, oven dried at 120° C. for 24 hours, is added tetrahydrofuran (300 ml, THF) and crude diethylamine salt of Tri-6-APA (36 grams, 0.068 moles). The slurry/mixture is magnetically stirred under dry nitrogen or argon and cooled to −10° C. using a dry ice/alcohol bath.

One equivalent of triethylamine (6.9 grams, 9.5 ml) is added dropwise to the stirred mixture, followed by the slow (over 30 minutes), dropwise addition of ethyl chloroformate (8.7 grams, 7.6 ml), while the temperature is maintained at −10° C.

The reaction mixture is stirred at −10° C. for two (2) hours, and then an aqueous solution of sodium azide (5.2 grams, 0.08 moles in 75 ml water) is poured into the reaction mixture and the temperature allowed to rise to 0° C.

The reaction mixture is stirred for 15 minutes at 0° C. and then cooled to −5° C. and subjected to the simultaneous addition of water (80 ml) and solid sodium borohydride (6.0 grams, 0.16 moles). The reaction slurry/mixture is stirred and allowed to warm to room temperature and stirred for 40 minutes at room temperature, before being extracted with methylene chloride (700 ml, CH$_2$Cl$_2$). The aqueous and CH$_2$Cl$_2$ layers are separated and the CH$_2$Cl$_2$ layer dried over anhydrous sodium sulfate (NA$_2$SO$_4$), filtered and the solvent removed under vacuum to yield 31 grams (89%) of crude alcohol.

Gravity chromatography, over silica gel, and elution with 20% (v/v) ethyl acetate: methylene chloride yields 17 grams of solid alcohol. 15 grams (43%) after trituration with cyclohexane.

H-NMR (CDCl$_3$, TMS, ppm): 7.5 (d,6H) 7.25 (m,9H) 4.42 (dd, 1H) 4.2 (d,1H) 3.9 (q,1H) 3.6 (m,1H) 3.4 (m,1H) 3.25 (d, 1H) 1.5 (s,3H) 1.3 (s,3H).

C. Preparation of 3,3 dimethyl-2-methanesulfonyloxymethyl-7-oxo-6-tritylamino-4-thia-1-azabicyclo[3.2.0]heptane (Tri-6-APCH2OSO2Me).

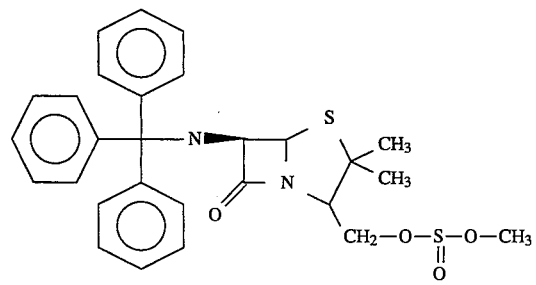

To a three-necked round bottom flask, oven dried at 120° C. for 24 hours and cooled under an argon atmosphere, is added pyridine (20 ml, 19.6 grams) and crude Tri-6-AP-CH2OH (2.0 grams, 0.0045 moles). The slurry/mixture is magnetically stirred under dry argon and cooled to 0 ° C. using an ice or dry ice/alcohol bath.

Methane sulfonyl chloride (0.57 grams, 0.84 ml) is slowly (5 minutes) added, dropwise, to the stirred mixture. The temperature is maintained at 0° C. and the reaction stirred for 30 minutes, allowed to warm to room temperature and then stirred for 3 hours at room temperature.

The reaction mixture is poured into ice water and the pH adjusted to four (4) using 10% aqueous phosphoric acid. This aqueous solution is extracted with diethylether (2×150 ml), the ether extracts washed with water, twice, and the ether dried over sodium sulfate (Na$_2$SO$_4$), filtered and removed under vacuum to yield 2.1 grams of crude mesylate.

Chromatography over silica gel and elution with 15% ethyl acetate (EtOAc): methylene chloride yields 1.3 grams of product.

H-NMR (CDCl$_3$, TMS ppm): 7.5 (d,6H) 7.30 (m,9H) 6.52 (d, 1H) 5.75 (q,1H) 5.4 (d,1H) 4.3 (m,1H) 4.2 (m,1H) 4.05 (t,1H) 3.1 (s,3H) 1.49 (s,3H) 1.25 (s,3H).

D. Preparation of 3,3 dimethyl-2-iodomethyl-7-oxo-6-tritylamino-4-thia-1-azabicyclo[3.2.0]heptane (Tri-6-AP-CH2I).

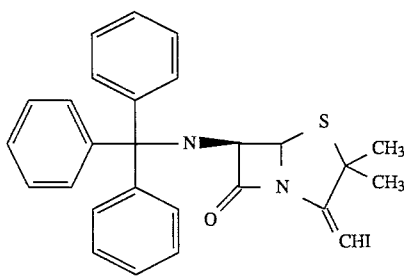

To a single-necked round bottom flask (100 ml), oven dried at 120° C. for 24 hours and cooled under an argon atmosphere, is added methyl ethyl ketone (35 ml), sodium iodide (0.016 moles) and sodium carbonate (0.0226 moles). The slurry/mixture is magnetically stirred under dry argon at room temperature and crude tri-6-AP-CH2OSO2Me (2.3 grams, 0.0045 moles) is added in one portion and the reaction mixture refluxed for three (3) hours.

Upon cooling to room temperature, the solvent is evaporated under vacuum, and the residue slurried with water (100 ml) and ethyl acetate (100 ml, EtOAc). The aqueous layer is removed, in a separatory funnel, and the EtOAc layer washed once with water, once with brine, and dried over sodium sulfate ($Na_2SO_4$). The sodium sulfate is filtered off and the solvent removed under vacuum to yield 1.6 grams (88%) of crude, higher Rf, product.

Chromatography over silica gel and eluting with 1:1 methylene chloride: P-950 ligroine yielded 1.1 grams (60%) of product.

H-NMR ($CDCl_3$, TMS, ppm); 7.55 (d,6H) 7.3 (m,9H) 4.42 (m,1H) 4.2 (d,1H) 3.9 (m,1H) 3.6 (m,1H) 3.4 (m,1H) 3.24 (d,1H) 1.5 (s,3H) 1.3 (s,3H).

E. Preparation of 3,3 dimethyl-2-methylene-7-oxo-6-tritylamino-4-thia-1-azabicyclo[3.2.0]heptane, (Tri-6-AP=CH2).

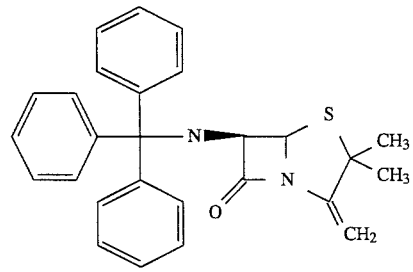

To a single-necked round bottom flask (50 ml), oven dried at 120° C. for 24 hours and cooled under an argon atmosphere, is added dimethylformamide (15 ml, DMF), sodium acetate (0.06 moles) and sodium carbonate (0.047 moles). The slurry/mixture is magnetically stirred under dry argon at room temperature and crude Tri-6-AP-CH2I (2.4 grams, 0.0045 moles) is added in one portion and the reaction mixture heated to 85°–90° C. for five (5) to six (6) hours.

The reaction progress is monitored by TLC analysis (5:4 p-950:methylene chloride) on silica gel and iodine vapor visualization. When the starting material is gone, by TLC analysis, the reaction mixture is cooled to 30° C. and the solids filtered off.

The filtrate is poured into ice water (70 ml) stirred for 15 minutes. The solids are filtered off, washed with water and air dried overnight to yield 2.2 grams of crude product.

Column chromatography over silica gel and elution with 5:4 p-950:methylene chloride yielded 1.6 grams of product.

HPLC analysis indicated one major peak, 99% by UV detection. IR (KBr, $cm^{-1}$): 747 (Ph) 1295 (OH) 1376 ($CH_3$) 1447 ($CH_2$) 1489 (Ph) 1641 (C=C) 1791 (C=O) 2867 (C-H) 3081 (=C-H) 3320 (N-H). MS (m/e): Large 426. H-NMR ($CDCL_3$, TMS, ppm): 7.5 (d,6H) 7.3 (m,9H) 4.8 (s,1H) 4.5 (m,1H) 4.4 (s,1H) 4.35 (m,1H) 3.0 (m,1H) 1.49 (s,3H) 1.42 (s,3H).

By analogous methods the following compounds can be synthesized:

a (5R,6R)-3,3-dimethyl-2-methylene-7-oxo-6-[(1,2,3,4-tetrahydro-2-naphthalenylcarbonyl)amino]-4-thia-1-azabicyclo[3.2.0]heptane;

b (5R,6R)-3,3-dimethyl-2-methylene-7-oxo-6-[(1-oxopropyl)amino]-4-thia-1-azabicyclo[3.2.0]heptane;

c (5R,6R)-3,3-dimethyl-2-methylene-7-oxo-6-[(1-oxobutyl)amino]-4-thia-1-azabicyclo[3.2.0]heptane;

d (5R,6R)-3,3-dimethyl-2-methylene-7-oxo-6-[(1-oxopentyl)amino]-4-thia-1-azabicyclo[3.2.0]heptane;

e (5R,6R)-3,3-dimethyl-2-methylene-7-oxo-6-[(1-oxohexyl)amino]-4-thia-1-azabicyclo[3.2.0]heptane;

f (5R,6R)-3,3-dimethyl-2-methylene-7-oxo-6-[(1-oxoheptyl)amino]-4-thia- 1-azabicyclo[3.2.0]heptane;

g (5R, 6R)-3,3-dimethyl-2-methylene7-oxo-6-[(1-oxo-octyl)amino]-4-thia-1-azabicyclo[3.2.0]heptane;

h (5R,6R)-3,3-dimethyl-2-methylene-7-oxo-6-[[1-oxo-2,2dimethyl-4-(2',5'-dimethylphenoxy) butyl]amino]-4-thia-1-azabicyclo[3.2.0]heptane;

i (5R,6R)-3,3-dimethyl-2-methylene-7-oxo-6-[[1-oxo-2,2-dimethyl-2(4-cyclopropylphenoxy)ethyl]amino]-4-thia-1-azabicyclo[3.2.0]heptane;

j (5R,6R)-3,3-dimethyl-2-methylene-7-oxo-6-[[(3,4-cycloheptenophenyl)carbonyl] amino]-4-thia-1-azabicyclo [3.2.0]heptane;

k (5R,6R)-3,3-dimethyl-2-methylene-7-oxo-6-[[(1,2,3,4-tetrahydronaphthalen- 6-yl )carbonyl]amino]-4-thia-1-azabicyclo[3.2.0]heptane;

l (5R,6R)-3,3-dimethyl-2-methylene-7-oxo-6-[[(cyclohexyl)carbonyl]amino]-4-thia-1-azabicyclo[3.2.0]heptane;

m (5R,6R)-3,3-dimethyl-2-methylene-7-oxo-6-(phenylacetyl)amino-4-thia-1-azabicyclo[3.2.0]heptane;

n (5R,6R)-3,3-dimethyl-2-methylene- 7-oxo-6-[(1-oxo-3-phenyl-propyl)amino]-4-thia-1-azabicyclo[3.2.0]heptane;

o (5R,6R)-3,3-dimethyl-2-methylene-7-oxo-6-[(1-oxo-4-phenylbutyl)amino]-4-thia-1-azabicyclo[3.2.0]heptane;

p (5R,6R)-3,3-dimethyl-2-methylene-7-oxo-6-[(1-oxo-5-phenylpentyl)-amino]-4-thia-1-azabicyclo[3.2.0]heptane;

q (5R,6R)-3,3-dimethyl-2-methylene-7-oxo-6-[(1-oxo-6-phenylhexyl)amino]-4-thia-1-azabicyclo[3.2.0]heptane;

r (5R,6R)-3,3-dimethyl-2-methylene-7-oxo-6-[(1-oxo-7-phenylheptyl)amino]-4-thia-1-azabicyclo[3.2.0]heptane;

s (5R,6R)-3,3-dimethyl-2-methylene-7-oxo-6-[(1-oxo-8-phenyloctyl)amino]-4-thia-1-azabicyclo [3.2.0]heptane;

t (5R, 6R)-3,3-dimethyl-2-methylene-7-oxo-6-[(1-oxo-9-phenylnonyl)-amino]-4-thia-1-azabicyclo[3.2.0]heptane;

u (5R,6R)-3,3-dimethyl-2-methylene-7-oxo-6-[(2-naphthalenylcarbonyl)-amino]-4-thia-1-azabicyclo[3.2.0]heptane;

v (5R, 6R )-3,3-dimethyl-2-methylene-7-oxo-6-[(3'-phenoxyphenylcarbonyl)-amino]-4-thia-1-azabicyclo[3.2.0]heptane;

w (5R, 6R)-3,3-dimethyl-2-methylene-7-oxo-6-[(2-anthracenylcarbonyl)-amino]-4-thia-1-azabicyclo [3.2.0]heptane;

x (5R,6R)-3,3-dimethyl-2-methylene-7-oxo-6-(1,1-dimethyl-2,2,2-triphenylethyl)amino-4-thia-1-azabicyclo [3.2.0]heptane;

y (5R,6R)-3,3-dimethyl-2-methylene-7-oxo-6-[(1,1-diethylpropyl)amino]-4-thia-1-azabicyclo[3.2.0]heptane;

z  (5R,6R)-3,3-dimethyl-2-methylene-7-oxo-6-[[[(3'-phenoxy)phenyl-1,1-dimethyl]methyl]amino]-4-thia-1-azabicyclo[3.2.0]heptane;
aa (5R,6R)-3,3-dimethyl-2-methylene-7-oxo-6-[(N-methyl-N-triphenylmethyl)amino]-4-thia-1-azabicyclo[3.2.0] heptane;
ab (5R,6R)-3,3-dimethyl-2-methylene-7-oxo-6-[[[1,1-(di-2-naphthalenyl)-1-(1-naphthalenyl)]methyl]amino]-4-thia-1-azabicyclo[3.2.0]heptane;
ac (5R,6R)-3,3-dimethyl-2-methylene-7-oxo-6-[(N-methyl-N-propyl)amino]-4-thia-1-azabicyclo[3.2.0]heptane;
ad (5R,6R)-3,3-dimethyl-2-methylene-7-oxo-6-[(N-methyl-N-butyl)amino]-4-thia-1-azabicyclo[3.2.0]heptane;
ae (5R,6R)-3,3-dimethyl-2-methylene-7-oxo-6-[(N-methyl-N-pentyl)amino]-4-thia-1-azabicyclo[3.2.0]heptane;
af (5R,6R)-3,3-dimethyl-2-methylene-7-oxo-6-[(N-methyl-N-hexyl)amino]-4-thia-1-azabicyclo[3.2.0]heptane;
ag (5R,6R)-3,3-dimethyl-2-methylene-7-oxo-6-[(N-methyl-N-heptyl)amino]-4-thia-1-azabicyclo[3.2.0]heptane;
ah (5R,6R)-3,3-dimethyl-2-methylene-7-oxo-6-[(N-methyl-N-octyl)amino]-4-thia-1-azabicyclo[3.2.0]heptane;
ai (5R,6R)-3,3-dimethyl-2-methylene-7-oxo-6-[(N-propyl)amino]-4-thia-1-azabicyclo[3.2.0]heptane;
aj (5R,6R)-3,3-dimethyl-2-methylene-7-oxo-6-[(N-butyl)amino]-4-thia-1-azabicyclo[3.2.0]heptane;
ak (5R,6R)-3,3-dimethyl-2-methylene-7-oxo-6-[(N-pentyl)amino]-4-thia-1-azabicyclo[3.2.0]heptane;
al (5R,6R)-3,3-dimethyl-2-methylene-7-oxo-6-[(N-hexyl)amino]-4-thia-1-azabicyclo[3.2.0]heptane;
am (5R,6R)-3,3-dimethyl-2-methylene-7-oxo-6-[(N-heptyl)amino]-4-thia-1-azabicyclo[3.2.0]heptane;
an (5R,6R)-3,3-dimethyl-2-methylene-7-oxo-6-[(N-octyl)amino]-4-thia-1-azabicyclo[3.2.0]heptane; and
ao (5R,6R)-3,3-dimethyl-2-methylene-7-oxo-6-[2,2,2-triphenylacetoamino]-4-thia-1-azabicyclo[3.2.0]heptane.

EXAMPLE 2

The compound of Example 1 is tested to determine its effect on pancreatic cholesterol esterase activity using p-nitrophenyl acetate (PNPA) as a substrate.

Purified pancreatic cholesterol esterase or ester hydrolase (PCH), shown by SDS-acrylamide and isoelectric focusing electrophoresis to be homogeneous, is used in a fresh solution of 90 mM (PNPA) in methanol.

The compound to be tested is dissolved and diluted in DMSO (dimethylsulfoxylene) to bring each assay mixture to the same concentration of compound and DMSO.

First an initial screen is conducted as follows: to determine the effect of an inhibitor on the rate of enzyme catalyzed hydrolysis of PNPA, enzyme and inhibitor are first incubated at room temperature for ten minutes. Following incubation, enough PNPA substrate to give a final concentration of 0.225 mM is added. The rate of PNPA hydrolysis is monitored by observing an increase of absorption at 405 nm over the course of ten minutes. On average, the concentration of inhibitor is 1300-fold greater than that of the enzyme inhibitor concentrate. The maximum solubility of PNPA of approximately twice the value of $K_m$, limited the accuracy the $K_M$ determination for the PNPA substrate. The estimated KM based on a nonlinear fit to the rate-progress curve is $K_M \sim$ 1 mM. With this estimate the substrate concentration used in the screen was approximately 0.25 $K_M$.

All assays are carried out in duplicate. Results for an incubation performed without addition of enzyme or inhibitor is used to correct for the rate of uncatalyzed hydrolysis of PNPA.

The results of the initial screen are presented in Table 1 along with additional enzyme specificity data which will be discussed below. The column identified for PCEH shows the percentage reduction in reaction velocity compared to the rate of the enzyme catalyzed reaction with no inhibitor present.

TABLE 1

| Inhibitor | | Degree of Inhibition | | | |
|---|---|---|---|---|---|
| Identification | Conc. mM | Percentage Reduction in Activity | | | |
| | | PCEH* | Chymotrypsin | Trypsin | PPE |
| Example 1 | 3.06 | 100 | 100 | 72 | 9 |

*The value shown indicates the percentage reduction in PNPA hydrolysis activity when compared to the rate of the hydrolytic reaction in the absence of inhibitor.

Specificity: An indication of inhibitor specificity is obtained by comparing the activity of three digestive system proteases in the presence and absence of the respective inhibitors. In these experiments approximately the same concentrations of inhibitor used in the PCEH experiments is used in assaying bovine chymotrypsin, bovine trypsin and porcine elastase. The conditions used in the protease assays are summarized in Table 2 and the percentage reduction in activity is summarized in Table 1.

TABLE 2

| | Protease Assay Conditions | | |
|---|---|---|---|
| | Chymotrypsin | Trypsin | PPE |
| Enzyme Conc. | 6.0 nM | 3.2 nM | 8.4 nM |
| Substrate | Suc-AAPF-p-NA | N-Chz-GPR-p-NA | Suc-AAPL-p-NA |
| Substrate Conc. | 0.3 mM | 0.2 mM | 4.7 mM |
| Inhibitor | | | |
| Example 1 | 3.1 μM | 4.6 μM | 3.1 μM |

The buffer used is the same for each protease; HEPES, 50 mM, pH 7.8.

$K_i$ Estimation: The rate of the PCEH catalyzed reaction is measured for six substrate concentrations ranging from 0.05 mM to 2.0 mM with and without inhibitor present. The three concentrations of inhibitor used in each $K_i$ determination are summarized in Table 3. The following controls are also carried out: 1) no inhibitor, no enzyme substrate only, 2) no inhibitor, DMSO, with PCEH. The limited solubility of the PNPA substrate limited the maximum concentration of substrate to $2 \times K_M$. The apparent $K_I$ for each inhibitor is summarized in Table 3.

TABLE 3

| | Inhibitor Concentrations and $K_i$ From PNPA Assays | | | | | |
|---|---|---|---|---|---|---|
| Inhibitor | Conc1 | $K_i(1)$ | Conc2 | $K_i(2)$ | Conc3 | $K_i(1)$ | $K_i$AVE |
| Example 1 | 4.3 | 4.8 ± 0.4 | 6.5 | 5.16 ± 0.9 | 13 | 5.60 ± 0.4 | 5.18 ± 0.4 |

Obviously, numerous modifications and variations of the present invention are possible in light of the above teachings. It is therefore to be understood that within the scope of the appended claims, the invention may be practiced otherwise than as specifically described herein.

We claim:

1. A compound of the formula:

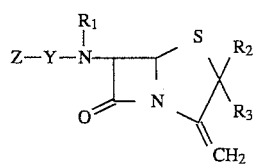

wherein $R_1$ is H or $C_{1-3}$ alkyl;
$R_2$ is H or $C_{1-3}$ alkyl;
$R_3$ is H or $C_{1-3}$ alkyl;
Y is a chemical bond

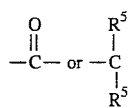

wherein $R_5$ is $C_{1-3}$ alkyl;

Z is $C_{1-6}$ alkyl, $C_{3-8}$ cyclo alkyl, phenyl phenyl $C_{1-6}$ alkyl, phenyloxy $C_{1-6}$ alkyl, bicyclic aryl, fused cyclo $C_{3-8}$ alkyl phenyl, fused phenyl cyclo $C_{3-8}$ alkyl, tricyclic aryl, phenoxyphenyl, or

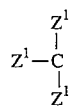

wherein each $Z^1$ is phenyl or bicyclic aryl, and wherein any of the ring structures can be mono- or di-substituted with $C_{1-3}$ alkyl or $C_{3-8}$ cyclo alkyl;

and a pharmaceutically acceptable salt thereof.

2. Compounds of claim 1 having the structure

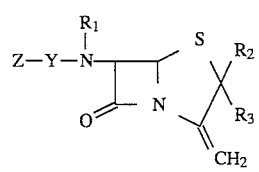

3. A compound of claim 2 being a (5R,6R)-3,3-dimethyl-2-methylene-7-oxo-6-[(1,2,3,4-tetrahydro-2-naphthalenylcarbonyl)amino]-4-thia-1-azabicyclo[3.2.0]heptane;

b (5R,6R)-3,3-dimethyl-2-methylene-7-oxo-6-[(1-oxopropyl)amino]-4-thia-1-azabicyclo[3.2.0]heptane;

c (5R,6R)-3,3-dimethyl-2-methylene-7-oxo-6-[(1-oxobutyl)amino]-4-thia-1-azabicyclo[3.2.0]heptane;

d (5R,6R)-3,3-dimethyl-2-methylene-7-oxo-6-[(1-oxopentyl)amino]-4-thia-1-azabicyclo[3.2.0]heptane;

e (5R,6R)-3,3-dimethyl-2-methylene-7-oxo-6-[(1-oxohexyl)amino]-4-thia-1-azabicyclo[3.2.0]heptane;

f (5R,6R)-3,3-dimethyl-2-methylene-7-oxo-6-[(1-oxoheptyl)amino]-4-thia-1-azabicyclo[3.2.0]heptane;

g (5R,6R)-3,3-dimethyl-2-methylene-7-oxo-6-[(1-oxooctyl)amino]-4-thia-1-azabicyclo[3.2.0]heptane;

h (5R,6R)-3,3-dimethyl-2-methylene-7-oxo-6-[[1-oxo-2,2-dimethyl-4-(2',5'-dimethylphenoxy)butyl]amino]-4-thia-1azabicyclo[3.2.0]heptane;

i (5R,6R)-3,3-dimethyl-2-methylene-7-oxo-6-[[1-oxo-2,2-dimethyl-2(4'-cyclopropylphenoxy)ethyl]amino]-4-thia-1-azabicyclo[3.2.0]heptane;

j (5R,6R)-3,3-dimethyl-2-methylene-7-oxo-6-[[(3,4-cycloheptenophenyl)carbonyl]amino]-4-thia-1-azabicyclo[3.2.0]heptane;

k (5R,6R)-3,3-dimethyl-2-methylene-7-oxo-6-[[(1,2,3,4-tetrahydronaphthalen-6-yl)carbonyl]amino]-4-thia-1-azabicyclo[3.2.0]heptane;

l (5R,6R)-3,3-dimethyl-2-methylene-7-oxo-6-[[(cyclohexyl)carbonyl]amino]-4-thia-1-azabicyclo[3.2.0]heptane;

m (5R,6R)-3,3-dimethyl-2-methylene-7-oxo-6-(phenylacetyl)amino-4-thia-1-azabicyclo[3.2.0]heptane;

n (5R,6R)-3,3-dimethyl-2-methylene-7-oxo-6-[(1-oxo-3-phenylpropyl)amino]-4-thia-1-azabicyclo[3.2.0]heptane;

o (5R,6R)-3,3-dimethyl-2-methylene-7-oxo-6-[(1-oxo-4-phenylbutyl)amino]-4-thia-1-azabicyclo[3.2.0]heptane;

p (5R,6R)-3,3-dimethyl-2-methylene-7-oxo-6-[(1-oxo-5-phenylpentyl)-amino]-4-thia-1-azabicyclo[3.2.0]heptane;

q (5R,6R)-3,3-dimethyl-2-methylene-7-oxo-6-[(1-oxo-6-phenylhexyl)-amino]-4-thia- 1-azabicyclo[3.2.0]heptane;

r (5R,6R)-3,3-dimethyl-2-methylene-7-oxo-6-[(1-oxo-7-phenylheptyl)-amino]-4-thia-1-azabicyclo[3.2.0]heptane;

s (5R,6R)-3,3-dimethyl-2-methylene-7-oxo-6-[(1-oxo-8-phenyloctyl)amino]-4-thia-1-azabicyclo[3.2.0]heptane;

t (5R,6R)-3,3-dimethyl-2-methylene-7-oxo-6-[(1-oxo-9-phenylnonyl)-amino]-4-thia-1-azabicyclo[3.2.0]heptane;

u (5R,6R)-3,3-dimethyl-2-methylene-7-oxo-6-[(2-naphthalenylcarbonyl)-amino]-4-thia-1-azabicyclo[3.2.0]heptane;

v (5R,6R)-3,3-dimethyl-2-methylene-7-oxo-6-[(3'-phenoxyphenylcarbonyl)-amino]-4-thia-1-azabicyclo

[3.2.0]heptane;

w   (5R,6R)-3,3-dimethyl-2-methylene-7-oxo-6-[(2-anthracenylcarbonyl)-amino]-4-thia-1-azabicyclo[3.2.0]heptane;

x   (5R,6R)-3,3-dimethyl-2-methylene-7-oxo-6-(1,1-dimethyl-2,2,2-triphenylethyl)amino-4-thia-1-azabicyclo[3.2.0]heptane;

y   (5R,6R)-3,3-dimethyl-2-methylene-7-oxo-6-[(1,1-diethylpropyl)amino]-4-thia-1-azabicyclo[3.2.0]heptane;

z   (5R,6R)-3,3-dimethyl-2-methylene-7-oxo-6-[[[(3'-phenoxy)phenyl-1,1-dimethyl]methyl]amino]-4-thia-1-azabicyclo[3.2.0]heptane;

aa  (5R,6R)-3,3-dimethyl-2-methylene-7-oxo-6-[(N-methyl-N-triphenylmethyl)amino]-4-thia-1-azabicyclo[3.2.0]heptane;

ab  (5R,6R)-3,3-dimethyl-2-methylene-7-oxo-6-[[[1,1-(di-2'-naphthalenyl)-1-(1'-naphthalenyl)]methyl]amino]-4-thia-1-azabicyclo[3.2.0]heptane;

ac  (5R,6R)-3,3-dimethyl-2-methylene-7-oxo-6-[(N-methyl-N-propyl)amino]-4-thia-1-azabicyclo[3.2.0]heptane;

ad  (5R,6R)-3,3-dimethyl-2-methylene-7-oxo-6-[(N-methyl-N-butyl)amino]-4-thia-1-azabicyclo[3.2.0]heptane;

ae  (5R,6R)-3,3-dimethyl-2-methylene-7-oxo-6-[(N-methyl-N-pentyl)amino]-4-thia-1-azabicyclo[3.2.0]heptane;

af  (5R,6R)-3,3-dimethyl-2-methylene-7-oxo-6-[(N-methyl-N-hexyl)amino]-4-thia-1-azabicyclo[3.2.0]heptane;

ag  (5R,6R)-3,3-dimethyl-2-methylene-7-oxo-6-[(N-methyl-N-heptyl)amino]-4-thia-1-azabicyclo[3.2.0]heptane;

ah  (5R,6R)-3,3-dimethyl-2-methylene-7-oxo-6-[(N-methyl-N-octyl)amino]-4-thia-1-azabicyclo[3.2.0]heptane;

ai  (5R,6R)-3,3-dimethyl-2-methylene-7-oxo-6-[(N-propyl)amino]-4-thia-1-azabicyclo[3.2.0]heptane;

aj  (5R,6R)-3,3-dimethyl-2-methylene-7-oxo-6-[(N-butyl)amino]-4-thia-1-azabicyclo[3.2.0]heptane;

ak  (5R,6R)-3,3-dimethyl-2-methylene-7-oxo-6-[(N-pentyl)amino]-4-thia-1-azabicyclo[3.2.0]heptane;

al  (5R,6R)-3,3-dimethyl-2-methylene-7-oxo-6-[(N-hexyl)amino]-4-thia-1-azabicyclo[3.2.0]heptane;

am  (5R,6R)-3,3-dimethyl-2-methylene-7-oxo-6-[(N-heptyl)amino]-4-thia-1-azabicyclo[3.2.0]heptane; and an  (5R,6R)-3,3-dimethyl-2-methylene-7-oxo-6-[(N-octyl)amino]-4-thia-1-azabicyclo[3.2.0]heptane.

4. A compound of claim 2 being (5R,6R)-3,3-dimethyl-2-methylene-7-oxo-6-tritylamino-4-thia-1-azabicyclo[3.2.0]heptane, or (5R,6R)-3,3-dimethyl-2-methylene-7-oxo-6-[2,2,2-triphenylacetoamido-4-thia-1-azabicyclo[3.2.0]heptane.

5. A method of treating high serum cholesterol levels, the method comprising administering to a patient needing such treatment, a pharmaceutically effective amount of a compound of claim 1.

6. A method of treating high serum cholesterol levels, the method comprising administering to a patient needing such treatment a pharmaceutically effective amount of a compound of claim 2.

7. A method of treating high serum cholesterol level, the method comprising administering to a patient needing such treatment a pharmaceutically effective amount of a compound of claim 3.

8. A method of treating high serum cholesterol level, the method comprising administering to a patient needing such treatment a pharmaceutically effective amount of a compound of claim 4.

9. A pharmaceutical composition for the treatment of high cholesterol level, the pharmaceutical composition comprising a pharmaceutically effective amount of a compound of claim 1 and a pharmaceutically acceptable carrier.

10. A pharmaceutical composition for the treatment of high serum cholesterol levels, the pharmaceutical composition comprising a pharmaceutically effective amount of a compound of claim 2 and a pharmaceutically acceptable carrier.

11. A pharmaceutical composition for the treatment of high serum cholesterol levels, the pharmaceutical composition comprising a pharmaceutically effective amount of a compound of claim 3 and a pharmaceutically acceptable carrier.

12. A pharmaceutical composition for the treatment of high serum cholesterol levels, the pharmaceutical composition comprising a pharmaceutically effective amount of a compound of claim 4 and a pharmaceutically acceptable carrier.

* * * * *

UNITED STATES PATENT AND TRADEMARK OFFICE
CERTIFICATE OF CORRECTION

PATENT NO. : 5,474,993

DATED : December 12, 1995

INVENTOR(S) : Rubin et al.

It is certified that error appears in the above-identified patent and that said Letters Patent is hereby corrected as shown below:

Title page,

In the Abstract and in column 2, lines 5 and 40, correct the chemical structure as follows:

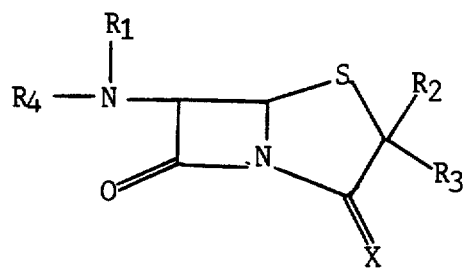

UNITED STATES PATENT AND TRADEMARK OFFICE
CERTIFICATE OF CORRECTION

PATENT NO. : 5,474,993
DATED : December 12, 1995
INVENTOR(S) : Rubin, et. al.

It is certified that error appears in the above-indentified patent and that said Letters Patent is hereby corrected as shown below:

In column 3, line 30, correct the chemical structure as follows:

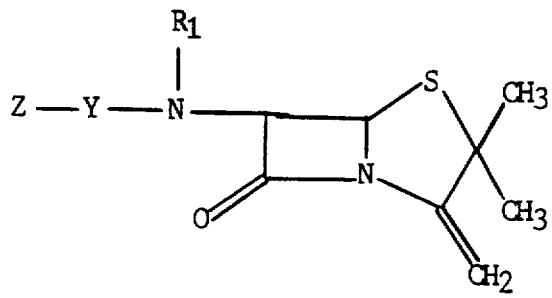

Signed and Sealed this

Nineteenth Day of November, 1996

Attest:

BRUCE LEHMAN

*Attesting Officer*     *Commissioner of Patents and Trademarks*